US011378648B2

(12) United States Patent
Xie et al.

(10) Patent No.: US 11,378,648 B2
(45) Date of Patent: Jul. 5, 2022

(54) LIVING OBJECT DETECTION METHOD AND APPARATUS AND ELECTRONIC DEVICE

(71) Applicant: FUJITSU LIMITED, Kawasaki (JP)

(72) Inventors: Lili Xie, Beijing (CN); Jun Tian, Beijing (CN); Hongchun Li, Beijing (CN); Qian Zhao, Beijing (CN)

(73) Assignee: FUJITSU LIMITED, Kawasaki (JP)

( * ) Notice: Subject to any disclaimer, the term of this patent is extended or adjusted under 35 U.S.C. 154(b) by 256 days.

(21) Appl. No.: 16/728,735

(22) Filed: Dec. 27, 2019

(65) Prior Publication Data
US 2020/0264273 A1    Aug. 20, 2020

(30) Foreign Application Priority Data

Feb. 19, 2019 (CN) .......................... 201910122519.X

(51) Int. Cl.
*G01S 7/35* (2006.01)
*G01S 13/32* (2006.01)
(Continued)

(52) U.S. Cl.
CPC .............. *G01S 7/352* (2013.01); *A61B 5/024* (2013.01); *A61B 5/05* (2013.01); *A61B 5/0507* (2013.01);
(Continued)

(58) Field of Classification Search
CPC ........ G01S 7/352; G01S 13/32; G01S 13/524; G01S 7/356; G01S 13/04; G01S 13/34;
(Continued)

(56) References Cited

U.S. PATENT DOCUMENTS

2004/0249258 A1* 12/2004 Tupin, Jr. ................ A61B 5/05
                                                      600/407
2015/0369911 A1* 12/2015 Mabrouk .............. G01S 13/888
                                                      342/159
(Continued)

FOREIGN PATENT DOCUMENTS

CN        105629228 A     6/2006
CN        102657530 A     9/2012
(Continued)

OTHER PUBLICATIONS

Extended European Search Report dated Jul. 27, 2020 in related European Patent Application No. 19217495.1-1206.
(Continued)

*Primary Examiner* — Donald H B Braswell
(74) *Attorney, Agent, or Firm* — Staas & Halsey LLP

(57) ABSTRACT

Embodiments of this disclosure provide a living object detection method and apparatus and electronic device. The apparatus includes a processor to calculate a distance matrix according to variance of Fourier transform amplitude values of radio signals received by a radio signal receiver within a determined period of time; and to calculate a distance between an object among objects and the radio signal receiver according to the distance matrix. According to this disclosure, a position of a living object among the objects may be detected based upon the distance in multiple scenarios.

10 Claims, 8 Drawing Sheets

(51) Int. Cl.
  *G01S 13/524* (2006.01)
  *G01S 13/04* (2006.01)
  *A61B 5/05* (2021.01)
  *A61B 5/0507* (2021.01)
  *A61B 5/024* (2006.01)

(52) U.S. Cl.
  CPC .............. *G01S 13/04* (2013.01); *G01S 13/32* (2013.01); *G01S 13/524* (2013.01); *A61B 2562/0228* (2013.01); *G01S 7/356* (2021.05)

(58) Field of Classification Search
  CPC ......... G01S 13/88; G01S 7/415; A61B 5/024; A61B 5/05; A61B 5/0507; A61B 2562/0228
  See application file for complete search history.

(56) References Cited

U.S. PATENT DOCUMENTS

2018/0120420 A1* 5/2018 McMahon ........... A61B 5/1128
2019/0011549 A1* 1/2019 Mercuri ................ G01S 13/726

FOREIGN PATENT DOCUMENTS

| CN | 106821347 A | 6/2017 |
| CN | 108663675 A | 10/2018 |
| EP | 3193189 A1 | 7/2017 |
| EP | 3360476 A1 | 8/2018 |
| EP | 3425419 A1 | 1/2019 |
| WO | WO 2017/156492 A1 | 9/2017 |

OTHER PUBLICATIONS

Marco Baldi, etc., "*Analysis and Simulation of Algorithms for Vital Signs Detection Using UWB Radars*"; 2011 IEEE International Conference on Ultra-Wideband (ICUWB); Dec. 31, 2011; (5 pages).

* cited by examiner

300

| | 1 | ...... | j-1 | j | j+1 | ...... | second distance index j → |
|---|---|---|---|---|---|---|---|
| 1 | H(1,1) | ...... | ...... | ...... | ...... | ...... | |
| ⋮ | ...... | ...... | ...... | ...... | ...... | ...... | |
| i-1 | ...... | ...... | H(i-1,j-1) | H(i-1,j) | H(i-1,j+1) | ...... | |
| i | ...... | ...... | H(i,j-1) | H(i,j) | H(i,j+1) | ...... | |
| i+1 | ...... | ...... | H(i+1,j-1) | H(i+1,j) | H(i+1,j+1) | ...... | |
| ⋮ | ...... | ...... | ...... | ...... | ...... | ...... | |

↓ first distance index i

FIG. 3

| | 1 | ...... | 12 | 13 | 14 | ...... | 34 | 35 | ...... |
|---|---|---|---|---|---|---|---|---|---|
| 1 | H(1,1) | ...... | ...... | ...... | ...... | ...... | ...... | ...... | ...... |
| ⋮ | ...... | ...... | ...... | ...... | ...... | ...... | ...... | ...... | ...... |
| 12 | ...... | ...... | 0 | 0.8141 | 0.8213 | ...... | ...... | ...... | ...... |
| 13 | ...... | ...... | 0.8141 | 0 | 0.9991 | ...... | ...... | ...... | ...... |
| 14 | ...... | ...... | 0.8213 | 0.9991 | 0 | ...... | ...... | ...... | ...... |
| ⋮ | ...... | ...... | ...... | ...... | ...... | ...... | ...... | ...... | ...... |
| 34 | ...... | ...... | ...... | ...... | ...... | ...... | 0 | 0.7500 | ...... |
| 35 | ...... | ...... | ...... | ...... | ...... | ...... | 0.7500 | 0 | ...... |
| ⋮ | ...... | ...... | ...... | ...... | ...... | ...... | ...... | ...... | ...... |

Second distance index j (→ columns)
first distance index i (↓ rows)

| | 1 | ...... | 12 | 13 | 14 | ...... | 34 | 35 | ...... |
|---|---|---|---|---|---|---|---|---|---|
| 1 | H(1,1) | ...... | ...... | ...... | ...... | ...... | ...... | ...... | ...... |
| ⋮ | ...... | ...... | ...... | ...... | ...... | ...... | ...... | ...... | |
| 12 | ...... | ...... | 0.7500 | 0.8141 | 0.8213 | ...... | ...... | ...... | ...... |
| 13 | ...... | ...... | 0.8141 | 0.7500 | 0.9991 | ...... | ...... | ...... | ...... |
| 14 | ...... | ...... | 0.8213 | 0.9991 | 0.7500 | ...... | ...... | ...... | ...... |
| ⋮ | ...... | ...... | ...... | ...... | ...... | ...... | ...... | ...... | |
| 34 | ...... | ...... | ...... | ...... | ...... | ...... | 0.7500 | 0.7500 | |
| 35 | ...... | ...... | ...... | ...... | ...... | ...... | 0.7500 | 0.7500 | |
| ⋮ | ...... | ...... | ...... | ...... | ...... | ...... | ...... | ...... | |

Second distance index j first distance index i

LIVING OBJECT DETECTION METHOD AND APPARATUS AND ELECTRONIC DEVICE

CROSS-REFERENCE TO RELATED APPLICATIONS

This application is based on and hereby claims priority under 35 USC 119 to Chinese Patent Application No. 201910122519.X, filed Feb. 19, 2019, in the China National Intellectual Property Administration, the entire contents of which are incorporated herein by reference.

TECHNICAL FIELD

This disclosure relates to the field of information technologies, and in particular to a living object detection method and apparatus and an electronic device.

BACKGROUND

Vital signs of living bodies, such as breathing and heartbeats, are important parameters and basis for medical treatment, health monitoring and search and rescue.

With the development of technologies, the non-contact vital sign detection technology has been developed. In the non-contact vital sign detection technology, vital sign detection may be realized without needing the object to wear any device. The object may be, for example, a human body or an animal body.

The vital sign detection technology based on radio signals is an important aspect of non-contact vital sign detection technology. In the radio signal-based vital sign detection technology, a radio signal transmission source may be used to transmit a radio signal, such as an electromagnetic wave, to the object, the radio signal being, for example, a radio signal based on a frequency modulated continuous wave (FMCW) modulation method, and the radio signal transmission source being, for example, a microwave radar, or the like.

It should be noted that the above description of the background is merely provided for clear and complete explanation of this disclosure and for easy understanding by those skilled in the art. And it should not be understood that the above technical solution is known to those skilled in the art as it is described in the background of this disclosure.

SUMMARY

In the radio signal-based vital sign detection technique, it usually needs to determine a position of the living object before performing the detection of the vital signs, that is, detection of the position of the living object.

It was found by the inventors that existing methods for detecting a position of a living object are applicable in limited scenarios. For example, for a target tracking-based detection method, the method is mostly applied to a scenario of a moving target, and is difficult to be applied to scenario of living object search and rescue and living object health monitoring; for a detection method based on an intensity of a reflected signal, the method is easy to be invalid for scenes where there exist a relatively large number of living bodies; and for a method for performing detection based on static background removal, the method is also easy to be invalid in a case of scenario change.

Embodiments of this disclosure provide a living object detection method and apparatus and electronic device. In the detection method, a distance between a living object and a radio signal receiver is detected according to variance of Fourier transform amplitude values of radio signals received by the radio signal receiver. As Fourier transform amplitude values of the received radio signals are able to reflect distance information, the variance of the amplitude values are able to reflect vital sign information of the living object. Hence, the method of the embodiments of this disclosure is less dependent on scenarios, and is able to detect a position of a static living object in multiple scenarios.

According to a first aspect of the embodiments of this disclosure, there is provided a living object detection apparatus, the apparatus including: a first calculating unit configured to calculate a distance matrix according to variance of Fourier transform amplitude values of radio signals received by the radio signal receiver within a predetermined period of time; and a second calculating unit configured to calculate a distance between a living object and the radio signal receiver according to the distance matrix; wherein the distance matrix has more than two elements, a value of each element denoting a probability of existence of a living object in a distance range to which the element corresponds, and the element having a first distance index and a second distance index, the distance range to which the element corresponds being a smaller one of distances greater than or equal to a distance to which the first distance index corresponds and a distance to which the second distance index corresponds, and a larger one of distances less than or equal to the distance to which the first distance index corresponds and the distance to which the second distance index corresponds. An apparatus to detect an object among objects as a living object according to radio signals received by a radio signal receiver, the apparatus comprising a processor to couple to a memory and to, calculate a distance matrix according to variance of Fourier transform amplitude values of the radio signals received by the radio signal receiver within a determined period of time; and calculate a distance between the object and the radio signal receiver according to the distance matrix; wherein the distance matrix has two or more elements, a value of each element denoting a probability indicative of existence of the living object in a distance range to which the element corresponds.

According to a second aspect of the embodiments of this disclosure, there is provided a living object detection method, in which a living object is detected according to radio signals received by a radio signal receiver, the method including: calculating a distance matrix according to variance of Fourier transform amplitude values of radio signals received by the radio signal receiver within a predetermined period of time; and calculating a distance between a living object and the radio signal receiver according to the distance matrix; wherein, the distance matrix has more than two elements, a value of each element denoting a probability of existence of a living object in a distance range to which the element corresponds, and the element having a first distance index and a second distance index, the distance range to which the element corresponds being a smaller one of distances greater than or equal to a distance to which the first distance index corresponds and a distance to which the second distance index corresponds, and a larger one of distances less than or equal to the distance to which the first distance index corresponds and the distance to which the second distance index corresponds.

According to a third aspect of the embodiments of this disclosure, there is provided an electronic device, including the living object detection apparatus as described in the first aspect.

An advantage of the embodiments of this disclosure exists in that the method is applicable in multiple scenarios to detect a position of a static living object.

With reference to the following description and drawings, the particular embodiments of this disclosure are disclosed in detail, and the principle of this disclosure and the manners of use are indicated. It should be understood that the scope of the embodiments of this disclosure is not limited thereto. The embodiments of this disclosure contain many alternations, modifications and equivalents within the scope of the terms of the appended claims.

Features that are described and/or illustrated with respect to one embodiment may be used in the same way or in a similar way in one or more other embodiments and/or in combination with or instead of the features of the other embodiments.

It should be emphasized that the term "comprise/include" when used in this specification is taken to specify the presence of stated features, integers, blocks or components but does not preclude the presence or addition of one or more other features, integers, blocks, components or groups thereof.

BRIEF DESCRIPTION OF THE DRAWINGS

The drawings are included to provide further understanding of this disclosure, which constitute a part of the specification and illustrate the preferred embodiments of this disclosure, and are used for setting forth the principles of this disclosure together with the description. It is obvious that the accompanying drawings in the following description are some embodiments of this disclosure, and for those of ordinary skills in the art, other accompanying drawings may be obtained according to these accompanying drawings without making an inventive effort. In the drawings:

FIG. 3 is a schematic diagram of a distance matrix of Embodiment 1 of this disclosure;

DETAILED DESCRIPTION OF THE DISCLOSURE

These and further aspects and features of this disclosure will be apparent with reference to the following description and attached drawings. In the description and drawings, particular embodiments of the disclosure have been disclosed in detail as being indicative of some of the ways in which the principles of the disclosure may be employed, but it is understood that the disclosure is not limited correspondingly in scope. Rather, the disclosure includes all changes, modifications and equivalents coming within the terms of the appended claims.

In the embodiments of this disclosure, terms "first", and "second", etc., are used to differentiate different elements with respect to names, and do not indicate spatial arrangement or temporal orders of these elements, and these elements should not be limited by these terms. Terms "and/or" include any one and all combinations of one or more relevantly listed terms. Terms "contain", "include" and "have" refer to existence of stated features, elements, components, or assemblies, but do not exclude existence or addition of one or more other features, elements, components, or assemblies.

In the embodiments of this disclosure, single forms "a", and "the", etc., include plural forms, and should be understood as "a kind of" or "a type of" in a broad sense, but should not defined as a meaning of "one"; and the term "the" should be understood as including both a single form and a plural form, except specified otherwise. Furthermore, the term "according to" should be understood as "at least partially according to", the term "based on" should be understood as "at least partially based on", except specified otherwise.

Embodiment 1

Embodiment 1 of this disclosure provides a living object detection apparatus.

In this embodiment, the living object detection apparatus may perform detection according to radio signals. Transmission and reception of the radio signals are performed by an apparatus for transceiving radio signals.

Figure 1:
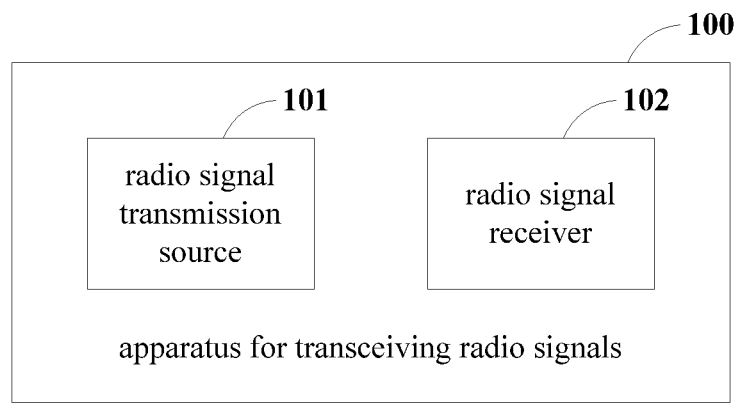
FIG. 1 is a schematic diagram of an apparatus for transceiving radio signals of Embodiment 1 of this disclosure.

FIG. 1 is a schematic diagram of the apparatus for transceiving radio signals. As shown in FIG. 1, an apparatus 100 for transceiving radio signals includes a radio signal transmission source 101 and a radio signal receiver 102.

In this embodiment, the radio signal transmission source 101 may transmit a radio signal, such as an electromagnetic wave, to an object, and the radio signal receiver 102 receives reflected signals formed by reflecting the radio signal by the object and other objects in an environment surrounding the object.

In this embodiment, the radio signal may be, for example, a radio signal based on a frequency modulation continuous wave (FMCW) modulation scheme. The radio signal transmission source 101 and the radio signal receiver 102 may be realized by, for example, a microwave radar, which may adopt, for example, a line array antenna array, or a planar array antenna array.

In one implementation, settings of parameters of the microwave radar may be as follows: a frame rate of a transmitted radio signal based on the FMCW modulation scheme is 15 to 25 Hz, a frame contains 64 to 256 chirp signals, a range resolution is 8~20 cm, a rate resolution is 0.05~0.15 m/s, and a ranging range is 5~10 m. It should be noted that the above parameter settings illustrative only, and this embodiment is not limited thereto.

In this embodiment, the living object may be, for example, a human body or an animal body, and vital signs of the living object may be, for example, a respiratory frequency and/or a heartbeat frequency.

Figure 2:
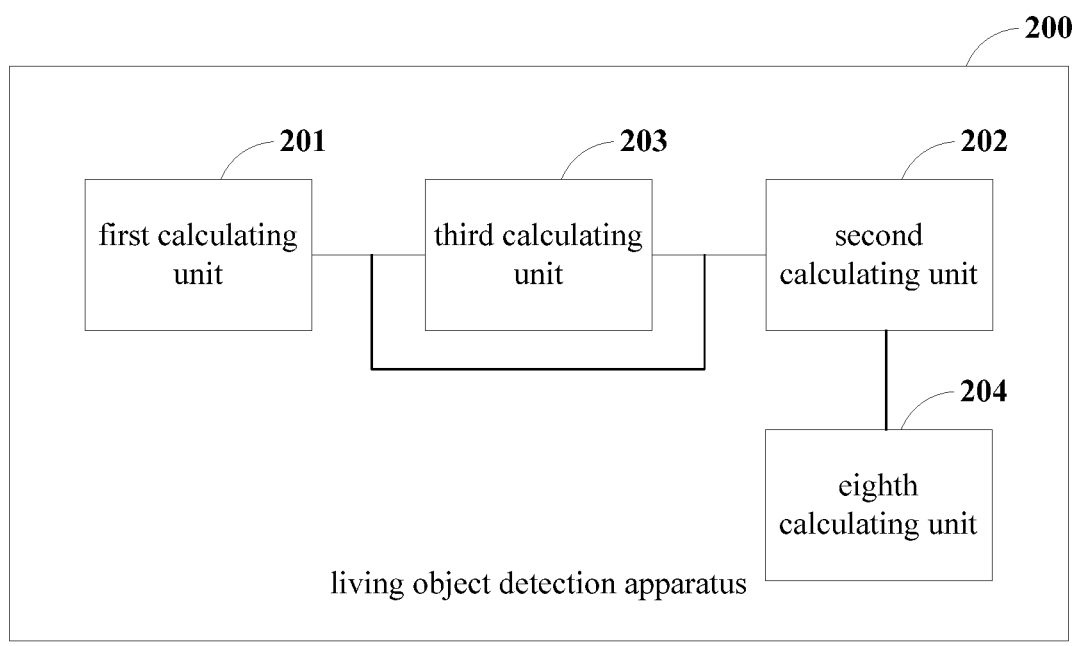
FIG. 2 is a schematic diagram of the living object detection apparatus of Embodiment 1 of this disclosure.

FIG. 2 is a schematic diagram of the living object detection apparatus of Embodiment 1. As shown in FIG. 2, a detection apparatus 200 may include a first calculating unit 201 and a second calculating unit 202.

In this embodiment, the first calculating unit 201 may calculate a distance matrix according to variance of Fourier transform amplitude values of radio signals received by the radio signal receiver within a predetermined period of time, and the second calculating unit 202 may calculate a distance between a living object and the radio signal receiver according to the distance matrix calculated by the first calculating unit 201.

In this embodiment, the Fourier transform amplitude values of the received radio signals may reflect information on a distance of a reflecting body of the radio signals and the radio signal receiver. When the reflecting body is a living object, the Fourier transform amplitude values will be changed along with vital signs of the living object. For example, breath of the living object causes fluctuant movement of the body so that the Fourier transform amplitude values of the received radio signals are changed, and the variance of Fourier transform amplitude values of the received radio signals may reflect information on the vital signs of the living object.

According to this embodiment, based on the variance of Fourier transform amplitude values of the received radio signals, a position of the living object in the static state may be detected, which is less dependent on scenarios, and is applicable to more scenarios.

In this embodiment, the radio signal receiver may be implemented by the radio signal receiver 102 of FIG. 1, that is, the radio signal receiver 102 transmits the received radio signals to the detection apparatus 200. Furthermore, radio signals may be transmitted by the radio signal transmission source 101 of FIG. 1, and the radio signals reflected by the reflecting body are received by the radio signal receiver.

In this embodiment, the detection device 200 and the apparatus 100 for transceiving radio signals may be integrally configured, for example, they are configured in an electronic device. Furthermore, the detection device 200 and the apparatus 100 for transceiving radio signals may be configured separately.

In this embodiment, the distance matrix calculated by the first calculating unit 201 may have more than two elements, a value of each element denoting a probability of existence of a living object in a distance range to which the element corresponds. For example, the value of the element may be greater than or equal to 0 and less than or equal to 1, and the larger the value of the element, the higher the probability of existence of a living object in the distance range.

FIG. 3 is a schematic diagram of the distance matrix. As shown in FIG. 3, an element in the distance matrix 300 may be denoted as H(i,j); where, i is a first distance index of the element, and j is a second distance index of the element, both i and j being integers greater than or equal to zero.

In the distance matrix 300, first distance indices i of elements of the same row are identical, second distance indices j of elements of the same column are identical, first distance indices of lower elements are greater than first distance indices of upper elements, and second distance indices of elements at the right side are greater than second distance indices of elements at the left side. Furthermore, the above order of sizes is not limited thereto, and it may also be that the first distance indices of the upper elements are greater than the first distance indices of the lower elements, and the second distance indices of the elements at the right side are less than the second distance indices of the elements at the left side.

A distance to which the first distance index i corresponds is that: a distance to the radio signal receiver is r*i. A distance to which the second distance index j corresponds is that: a distance to the radio signal receiver is r*j; where, r denotes a predetermined length, for example, the predetermined length r may be a distance resolution of the radio signal receiver.

The number of elements in the distance matrix 300 may be determined by a farthest distance that may be detected by the living object detection apparatus 200.

In this embodiment, as shown in FIG. 3, a range of the distance to which the element H(i,j) in the distance matrix 300 corresponds is: the distance between the living object and the radio signal receiver is greater than or equal to a smaller one of a distance to which the first distance index i corresponds and a distance to which the second distance index j corresponds, and the distance between the living object and the radio signal receiver is less than or equal to a larger one of the distance to which the first distance index i corresponds and the distance to which the second distance index j corresponds.

In this embodiment, the variance of the Fourier transform amplitude values of the received radio signals includes a standard deviation std_fftVal of the Fourier transform amplitude values of the received radio signals in a predetermined period of time.

In this embodiment, for the element H(i,j) in the distance matrix, the standard deviation to which the first distance index i corresponds may be expressed as std_fftVal(i).

For example, in the predetermined period of time, the radio signal receiver periodically receives the radio signals according to a predetermined period, and at each time the radio signals are received, the radio signal receiver performs Fourier transform on the received radio signals, and calculates the Fourier transform amplitude values at the distance to which first distance index i correspond. Assuming that the radio signals are received N times in the predetermined period of time and amplitude values of N pieces of Fourier transform are calculated and obtained for the first distance index i, the standard deviation std_fftVal(i) to which the first distance index i corresponds may be obtained by calculating a standard deviation of the amplitude values of the N pieces of Fourier transform.

Furthermore, a mean value of the Fourier transform amplitude values of the radio signals received in the predetermined period of time to which the first distance index i corresponds may be expressed as fftVal_mean(i); where, fftVal_mean(i) may be obtained by averaging the above amplitude values of the N pieces of Fourier transform.

In this embodiment, the standard deviation of the Fourier transform amplitude values of the received radio signals to which the second distance index j corresponds is expressed as std_fftVal(j), and a mean value of the Fourier transform amplitude values of the radio signals received in the predetermined period of time to which the second distance index j corresponds may be expressed as fftVal_mean(j). Reference may be made to the above description of std_fftVal(i) and fftVal_mean(i) for a calculation method of std_fftVal(j) and fftVal_mean(j).

In this embodiment, in a case where an absolute value of a difference between the first distance index i and the second distance index j is less than a predetermined value n and greater than 0, the first calculating unit 201 grants a predetermined value σ1 for the element H(i,j) in the distance matrix when at least one of the following conditions (1) and (2) is satisfied, for example, the predetermined value σ1 may be greater than 0 and less than or equal to 1.

The conditions (1) and (2) are:

$$\text{std\_fftVal}(i) > \theta 3, \text{ and std\_fftVal}(j) > \theta 3 \qquad \text{condition (1)},$$

$$\text{std\_fftratio}(i) > \beta 2, \text{ and std\_fftratio}(j) > \beta 2 \qquad \text{condition (2)}.$$

In condition (2), std_fftratio (i)=std_fftVal(i)/fftVal_mean (i), std_fftratio (j)=std_fftVal(j)/fftVal_mean(j).

Furthermore, in this embodiment, in a case where the absolute value of the difference between the first distance index i and the second distance index j is less than the predetermined value n, the first calculating unit 201 grants a predetermined value σ2 for the element H(i,j) in the distance matrix when neither the conditions (1) nor (2) is satisfied, the predetermined value σ2 is less than the predetermined value σ1, for example, the predetermined value σ2 is equal to 0.

Furthermore, in this embodiment, in a case where the absolute value of the difference between the first distance index i and the second distance index j is greater than or equal to the predetermined value n, the first calculating unit 201 may also grant the predetermined value σ2 for the element H(i,j) in the distance matrix.

In this embodiment, the predetermined value n may be set according to the distance resolution R of the radio signal receiver and a size of the living object in a direction of receiving the radio signals, for example, n≥T/R; where, T is, for example, 20 cm-30 cm.

In this embodiment, for each element H(i,j) in the distance matrix, the first calculating unit 201 may calculate a value of the element H(i,j) by using the above-described method. Thus, the distance matrix 300 is obtained after granting corresponding values for all the elements in the distance matrix.

In this embodiment, as shown in FIG. 2, the living object detection apparatus 200 may further include a third calculating unit 203.

The third calculating unit 203 is configured to, for an element in the distance matrix having the first distance index or the second distance index less than a first predetermined value, update a value of the element according to phase information of the received radio signal.

For example, for the element H(i,j) in the distance matrix 300, when i<the first predetermined value or j<the first predetermined value, the distance to which the first distance index corresponds or the distance to which the second distance index corresponds is less than a predetermined distance R0, and the third calculating unit 203 may update a value of the element H(i,j) according to phase information of the received radio signal.

In the case where a living object reflects the radio signals, the phase information of the radio signals received by the radio signal receiver is modulated by life activities of the living object, such as breath, or heartbeat, that is, slight movement of a body surface of the living object will produce offset to a phase of a specific frequency point of reflected signals. Hence, the phase information may reflect the vital sign information of the living object, and in a case where the living object is close to the radio signal receiver, the phase information of the radio signals is subjected to less interference, and the accuracy of the living object detection is higher.

In this embodiment, by providing the third calculating unit 203, the living object detection may be further performed based on the phase information of the received radio signals within a range close to the radio signal receiver, thereby improving the accuracy of the living object detection.

In this embodiment, the phase information of the received radio signals may include: a correlation Correlation (i,j) between a phase Phase(i) at a distance to which the first distance index corresponds and a phase Phase(j) at a distance to which the second distance index corresponds within the predetermined period of time, and/or, a standard deviation (std_Phase) of phases of the radio signals received within the predetermined period of time.

For example, for the element H(i,j) in the distance matrix 300, in the predetermined period of time, the radio signal receiver periodically receives the radio signals according to the predetermined period, and each time the radio signals are received, the radio signal receiver calculates, for the radio signals received at this time, the phase Phase(i) at the distance to which the first distance index i corresponds and the phase Phase(j) at the distance to which the second distance index j corresponds; assuming that the radio signals are received N times in the predetermined period of time, a sequence of a length N consisting of N phases Phase(i) and a sequence of a length N consisting of N phases Phase(j) are obtained, and a correlation of the two sequences may be denoted by Correlation (i,j), which be expressed by, for example, a correlation coefficient.

In this embodiment, for the element H(i,j) in the distance matrix 300, the standard deviation of the phase of the radio signals received in the predetermined period of time to which the first distance index i corresponds may be expressed as std_Phase(i).

For example, for the N phases Phase(i) corresponding to the first index i calculated for the radio signals received within the predetermined time period, standard deviation std_Phase(i) thereof is calculated.

In this embodiment, the standard deviation of the phase of the received radio signal corresponding to the second distance index j during the predetermined period of time may be expressed as std_Phase(j).

For example, for the N phases Phase(j) corresponding to the second index j calculated for the radio signals received within the predetermined time period, a standard deviation std_Phase(j) thereof is calculated.

In this embodiment, in a case where the absolute value of the difference between the first distance index i and the second distance index j is less than the predetermined value n and greater than 0, the third calculating unit 203 grants a value C denoting Correlation (i,j) for the element H(i,j) in the distance matrix when following condition (3) and at least one of conditions (4) and (5) are satisfied.

The conditions (3), (4) and (5) are:

$$\text{std\_fftVal}(i) > \theta 1, \text{ and std\_fftVal}(j) > \theta 1 \qquad \text{condition (3)},$$

$$\text{std\_Phase}(i) > \theta 2, \text{ and std\_Phase}(j) > \theta 2 \qquad \text{condition (4)},$$

$$C > \sigma \qquad \text{condition (5)}.$$

In condition (3), std_fftVal(i) and std_fftVal(j) respectively denote, in the predetermined period of time, standard deviations of Fourier transform amplitude values of the received radio signals to which the first distance index i and the second distance index j correspond respectively. Reference may be made to the description of the first calculating unit 201 for detailed description of std_fftVal(i) and std_fftVal(j).

Furthermore, in this embodiment, in a case where the absolute value of the difference between the first distance index i and the second distance index j is less than the predetermined value n, the third calculating unit 203 grants a predetermined value σ2 for the element H(i,j) in the distance matrix 300 when condition (3) is satisfied, neither conditions (4) nor (5) is satisfied, description of σ2 being the same as that given above.

Furthermore, in this embodiment, in a case where the absolute value of the difference between the first distance index i and the second distance index j is greater than or equal to the predetermined value n, or condition (3) is not satisfied, the third calculating unit 203 grants the predetermined value σ2 for the element H(i,j) in the distance matrix 300.

In this embodiment, for each element H(i,j) in the distance matrix that is in conformity with i<the first predetermined value or j<the first predetermined value, the third calculating unit 203 may update a value of the element H(i,j) by using the above methods, thereby obtaining an updated distance matrix 300.

In this embodiment, the second calculating unit 202 may calculate the distance between the living object and the radio signal receiver according to the distance matrix 300.

In one implementation, the second calculating unit 202 may be configured to update the elements in the distance matrix, and calculate the distance between the living object and the radio signal receiver based on the updated distance matrix.

The updating the elements in the distance matrix by the second calculating unit 202 may include: updating diagonal elements in the distance matrix, and updating elements of values equal to the predetermined value σ2 in the distance matrix.

In this embodiment, updating the diagonal elements in the distance matrix may include: if the element H (i,j)>σ2 and i and j are not equal, granting a seventh predetermined value σ to diagonal elements H (i,i) and H (j,j) to which the element corresponds in the distance matrix, thereby facilitating extraction of the element H(i,j) in batch processing.

In this embodiment, updating the elements of values equal to the predetermined value σ2 in the distance matrix may include: for the elements H(i,j) (i and j are unequal) of values equal to the predetermined value σ2 in the distance, updating values of the elements by using values of elements neighboring the elements.

In one implementation, when a value of an element is the predetermined value σ2 and the number of its neighboring elements with values greater than the predetermined value σ2 is greater than or equal to the predetermined value N1, a mean value of elements in the neighboring elements with values greater than the predetermined value σ2 is used to update the elements. Iterative updating may be performed on the distance matrix, until there is no element in the distance matrix satisfying the above updating conditions. Hence, a measurement error may be avoided.

For example, the element H (i,j)=σ2, i is not equal to j, and neighboring elements of H (i,j) are H (i−1, j), H (i+1, j), H (i, J−1) and H (i, j+1), if the number of elements in these neighboring elements with values greater than the predetermined value σ2 is greater than or equal to N1, a mean value of the elements in these neighboring elements with values greater than the predetermined value σ2 is used to update the value of the element H (i,j).

In this embodiment, updating may be performed first on the diagonal elements, and then updating may be performed on the elements having values equal to the predetermined value σ2.

In this embodiment, the second calculating unit 202 calculates the distance between the living object and the radio signal receiver based on the updated distance matrix, which may include, for example, when the number of pieces of continuous distribution of elements in the distance matrix having values greater than the predetermined value σ2 is greater than n/m, determining that there exists a living object in a distance range to which the continuously distributed elements correspond. The elements in the distance matrix having values greater than the predetermined value σ2 may be elements in the distance matrix having values greater than 0, and m may be a natural number less than n, for example, m is 2.

In this embodiment, the second calculating unit 202 may also not update the elements in the distance matrix, but directly calculate the distance between the living object and the radio signal receiver based on an un-updated distance matrix.

In this embodiment, as shown in FIG. 2, the living object detection apparatus 200 may further include an eighth calculating unit 204.

The eighth calculating unit 204 configured to determine the distance between the living object and the radio signal transceiver based on distances between the living object and the radio signal transceiver detected multiple predetermined periods of time.

In this embodiment, the predetermined period of time may be deemed as a time window, a length of the time window being of T seconds, the time window being a sliding window, and an overlapped time of two adjacent time windows being of, for example, 0.5 T. The eighth calculating unit 204 may determine the distance between the living object and the radio signal transceiver according to distances between the living object and the radio signal transceiver detected in the M time windows; where, M may be a natural number greater than or equal to 2.

In this embodiment, a range of a distance between the living object and the radio signal transceiver detected in an S-th time window is denoted by HP(S); where, S≤M. In a range of distances detected in multiple time windows, if a ratio of occurrence of the same distance range exceeds a threshold, it is determined that there exists a living object in the distance range; for example, in detection results in the M time windows, if a distance range occurs V times, V/M is a ratio of occurrence of the distance range; and if the ratio V/M exceeds a threshold, it is determined that there exists a living object within the distance range.

In this embodiment, if a distance between center positions of two distance ranges is not greater than n*R, it is determined that the two distance ranges are the same distance range; where, R denotes the distance resolution of the radio signal receiver.

Furthermore, in this embodiment, the detection apparatus 200 may output a union of the detection results in the M time windows, thereby improving a sensitivity of detecting a living object.

In this embodiment, if it is determined that there exist living bodies in more than two distance ranges, the living object detection apparatus 200 may output the more than two distance ranges, thereby being applicable to a scenario where there exist relatively large number of living bodies.

Figure 4:
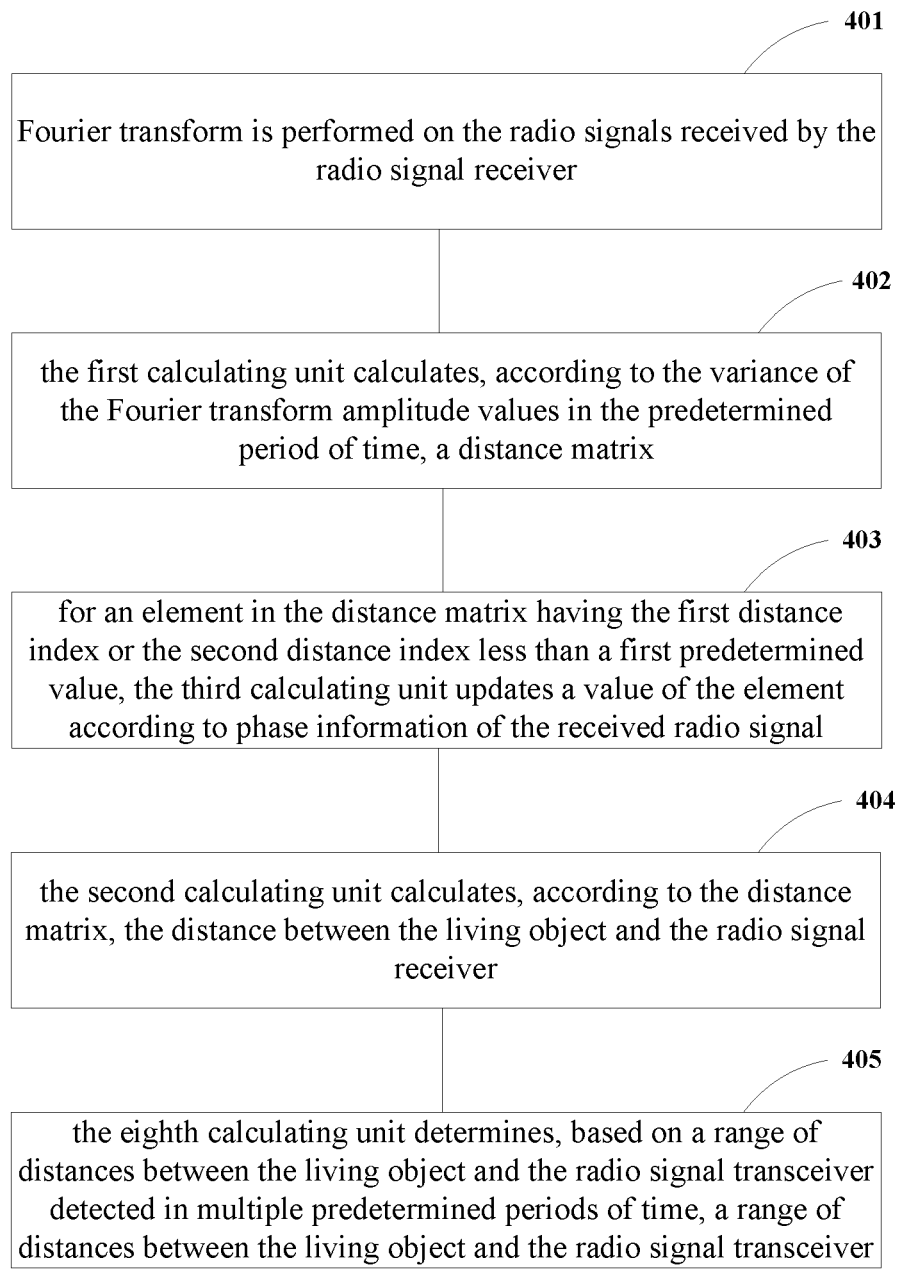
FIG. 4 is a schematic diagram of a workflow the living object detection apparatus of Embodiment 1 of this disclosure.

FIG. 4 is a schematic diagram of a workflow the living object detection apparatus of this embodiment. As shown in FIG. 4, the process includes:

block 401: Fourier transform is performed on the radio signals received by the radio signal receiver.

block 402: the first calculating unit calculates, according to the variance of the Fourier transform amplitude values in the predetermined period of time, a distance matrix;

block 403: for an element in the distance matrix having the first distance index or the second distance index less than a first predetermined value, the third calculating unit updates a value of the element according to phase information of the received radio signal;

block 404: the second calculating unit calculates, according to the distance matrix, the distance between the living object and the radio signal receiver; and block 405: the eighth calculating unit determines, based on a range of distances between the living object and the radio signal transceiver detected in multiple predetermined periods of time, a range of distances between the living object and the radio signal transceiver.

A method of performing detection by the living object detection apparatus of this embodiment shall be described below with reference to an example.

In this example, parameters are set as follows:

a frequency of a radio signal transmitted by the radio signal transmission source is 77 GHz;

a sampling frequency of the radio signal receiver is 20 Hz;

the radio signal transmission source and the radio signal receiver are disposed in a radar device, and two living bodies to be detected are respectively located statically at positions at distances about 1.6 m and 4.5 m from the radar device; R0=3 m, R=0.125 m, n=3, θ2=0.5, σ=0.75, θ1=θ3=30, β2=0.25, σ2=0, a time window taken as the predetermined period of time T=30S, an overlapped time of neighboring windows is 15 s, a total number of windows is 5, and length of time to which the 5 windows correspond is 90 s.

Figures 5, 6:
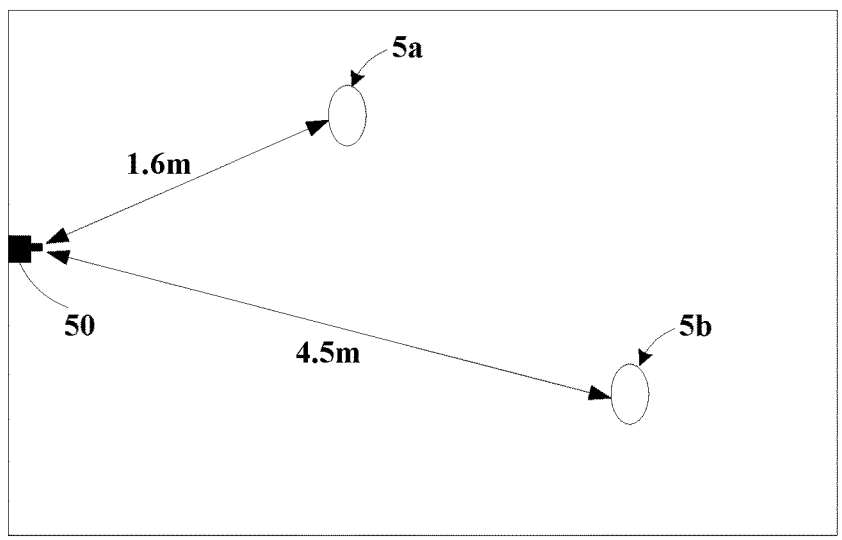
FIG. 5 is a schematic diagram of a relative position relationship between living objects to be detected and a radar device of Embodiment 1 of this disclosure.
FIG. 6 is a schematic diagram of a distance matrix to which a first time window corresponds of Embodiment 1 of this disclosure.

FIG. 5 is a schematic diagram of a relative position relationship between living objects 5a and 5b to be detected and a radar device 50.

Figures 7, 8:
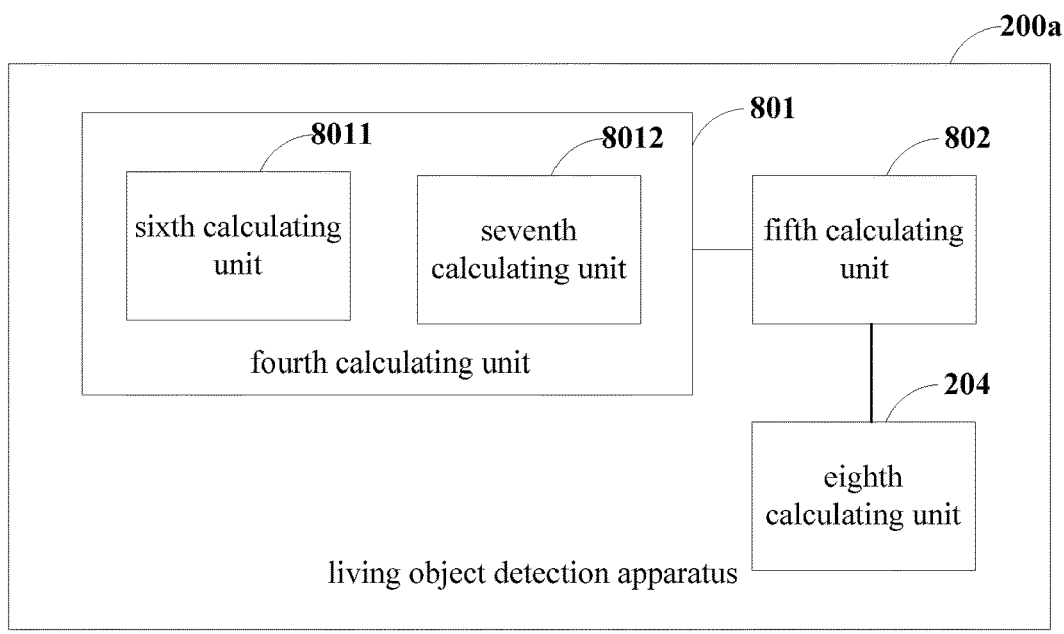
FIG. 7 is a schematic diagram of the distance matrix in FIG. 6 after being updated by a second calculating unit of Embodiment 1 of this disclosure.
FIG. 8 is another schematic diagram of the living object detection apparatus of Embodiment 1 of this disclosure.

FIG. 6 is a schematic diagram of a distance matrix to which a first time window corresponds, and FIG. 7 is a schematic diagram of the distance matrix in FIG. 6 after being updated by the second calculating unit.

The second calculating unit 202 outputs two ranges of a first position mark and a second position mark according to the distance matrix of FIG. 7, i.e. (12~14) and (34~35), indicating that there exist living bodies in distance ranges to which the two ranges correspond. The distance range to which the position mark 12~14 corresponds is 1.5 m~1.75 m, and the distance range to which the position mark 34~35 corresponds is 4.25 m~4.375 m.

Position marks respectively outputted by a second to a fifth time windows are:

the second window: (12~14), (34~35);
the third window: (12~15), (34~35);
the fourth window: (13~15), (34~35); and
the fifth window: (13~15), (34~35).

A finally outputted result is a union of multiple window ranges: (1.5 m~1.875 m) and (4.25 m~4.375 m). This output result is relatively close to an actual situation in FIG. 5.

In this embodiment, a living object detection apparatus 200a is further provided, which is a variant of the living object detection apparatus of FIG. 2.

FIG. 8 is a schematic diagram of the living object detection apparatus 200a. As shown in FIG. 8, the living object detection apparatus 200a includes a fourth calculating unit 801 and a fifth calculating unit 802.

The fourth calculating unit 801 calculates the distance matrix based on the variance of the Fourier transform amplitude values of the radio signals received by the radio signal receiver, or calculates a distance matrix based on phase information of the received radio signals, according to an estimated distance between a reflecting object of the radio signals and the radio signal receiver.

The fifth calculating unit 802 calculates the distance between the living object and the radio signal receiver according to the distance matrix.

Except that the fourth calculating unit 801 is different from the first calculating unit 201, other parts of the living object detection apparatus 200a and the living object detection apparatus 200 are identical. For example, functions executed by the fifth calculating unit 802 and the second calculating unit 202 of FIG. 2 may be identical, and the living object detection apparatus 200a may also include the eighth calculating unit 204, which shall not be described herein any further. Furthermore, description of the distance matrix is identical to that as described above.

According to the living object detection apparatus 200a of FIG. 8, different calculation methods may be used for different estimated distances, thereby improving accuracy of detection at a relatively close distance and improving a reliability of detection at a relatively far distance.

In this embodiment, as shown in FIG. 8, the fourth calculating unit 801 may include a sixth calculating unit 8011 and a seventh calculating unit 8012.

For a case where the estimated distance is greater than the predetermined distance R0, the sixth calculating unit 8011 calculates the distance matrix based on the variance of the Fourier transform amplitude values of the received radio signals; and for a case where the estimated distance is less than or equal to the predetermined distance R0, the seventh calculating unit 8012 calculates the distance matrix based on the phase information of the received radio signals. A complete distance matrix may be obtained by combining the distance matrix calculated by the sixth calculating unit 8011 and the distance matrix calculated by the seventh calculating unit 8012.

Figure 9:
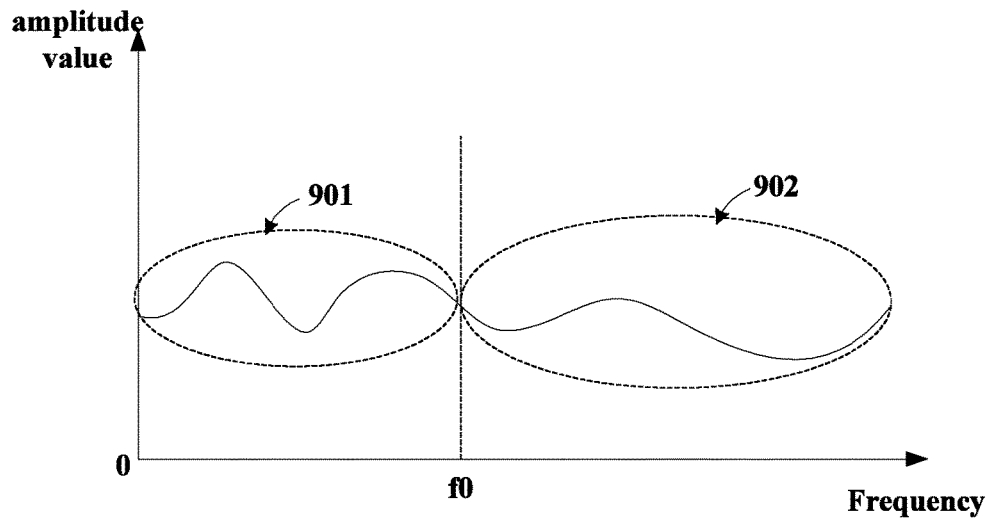
FIG. 9 is a schematic diagram of a result of Fourier transform of Embodiment 1 of this disclosure.

For example, Fourier transform may be performed on the radio signals received by the radio signal receiver, and FIG. 9 is a schematic diagram of a result of the Fourier transform. A frequency point f0 in FIG. 9 corresponds to the predetermined distance R0, signals 901 in FIG. 9 with frequency points less than or equal to f0 correspond to radio signals reflected by reflecting objects with estimated distances less than or equal to the predetermined distance R0, and the seventh calculating unit 8012 calculates the distance matrix based on phase information of the signals; and signals 902 in FIG. 9 with frequency points greater than f0 correspond to radio signals reflected by reflecting objects with estimated distances greater than the predetermined distance R0, and the sixth calculating unit 8011 is used to calculate the distance matrix based on variance of Fourier transform amplitude values of the signals.

In this embodiment, the sixth calculating unit 8011 calculates the distance matrix based on the variance of the Fourier transform amplitude values of the received radio signals, and a calculation method thereof is identical to that of the first calculating unit 201. The seventh calculating unit 8012 calculates the distance matrix based on the phase information of the received radio signals, and a calculation method thereof is identical to that of the third calculating unit 203.

Figure 10:
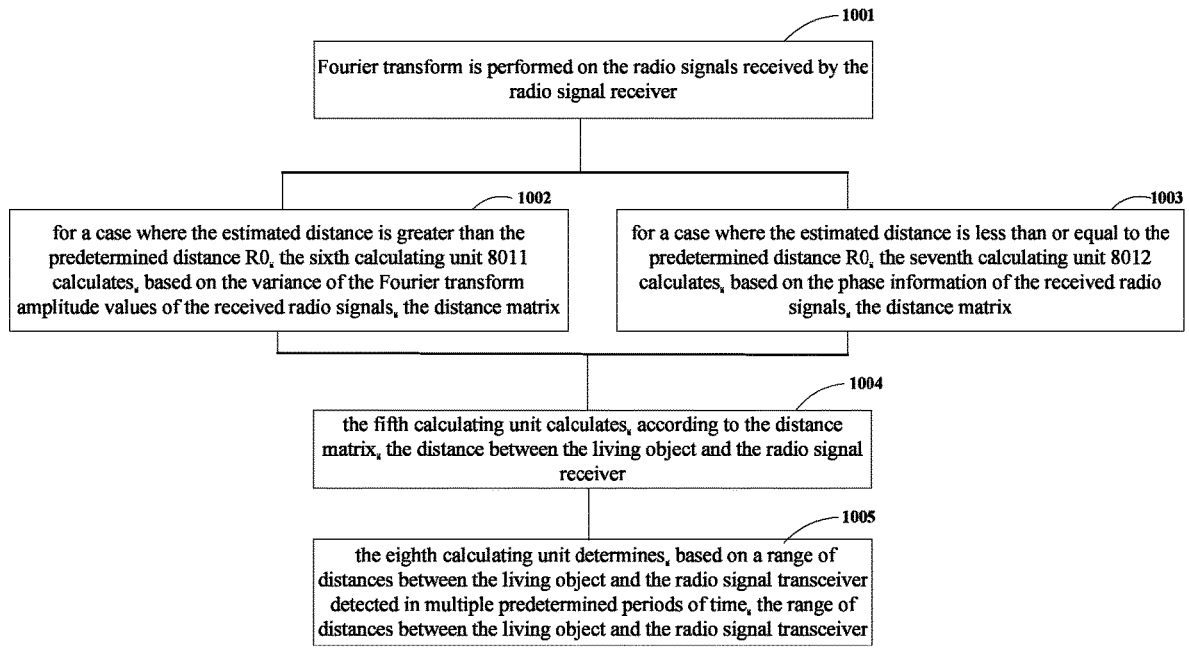
FIG. 10 is another schematic diagram of the workflow of the living object detection apparatus of Embodiment 1 of this disclosure.

FIG. 10 is another schematic diagram of the workflow of the living object detection apparatus of this embodiment. As shown in FIG. 10, the process includes:

block 1001: Fourier transform is performed on the radio signals received by the radio signal receiver;

block 1002: for a case where the estimated distance is greater than the predetermined distance R0, the sixth calculating unit 8011 calculates, based on the variance of the Fourier transform amplitude values of the received radio signals, the distance matrix;

block 1003: for a case where the estimated distance is less than or equal to the predetermined distance R0, the seventh calculating unit 8012 calculates, based on the phase information of the received radio signals, the distance matrix;

block 1004: the fifth calculating unit calculates, according to the distance matrix, the distance between the living object and the radio signal receiver.

block 1005: the eighth calculating unit determines, based on a range of distances between the living object and the radio signal transceiver detected in multiple predetermined periods of time, the range of distances between the living object and the radio signal transceiver.

According to this embodiment and its variant, a position of a static living object may be detected, which is less dependent on scenarios, and is applicable to relatively wide ranges of scenarios.

Embodiment 2

Embodiment 2 of this disclosure provides a living object detection method, corresponding to the living object detection apparatus of Embodiment 1.

Figure 11:
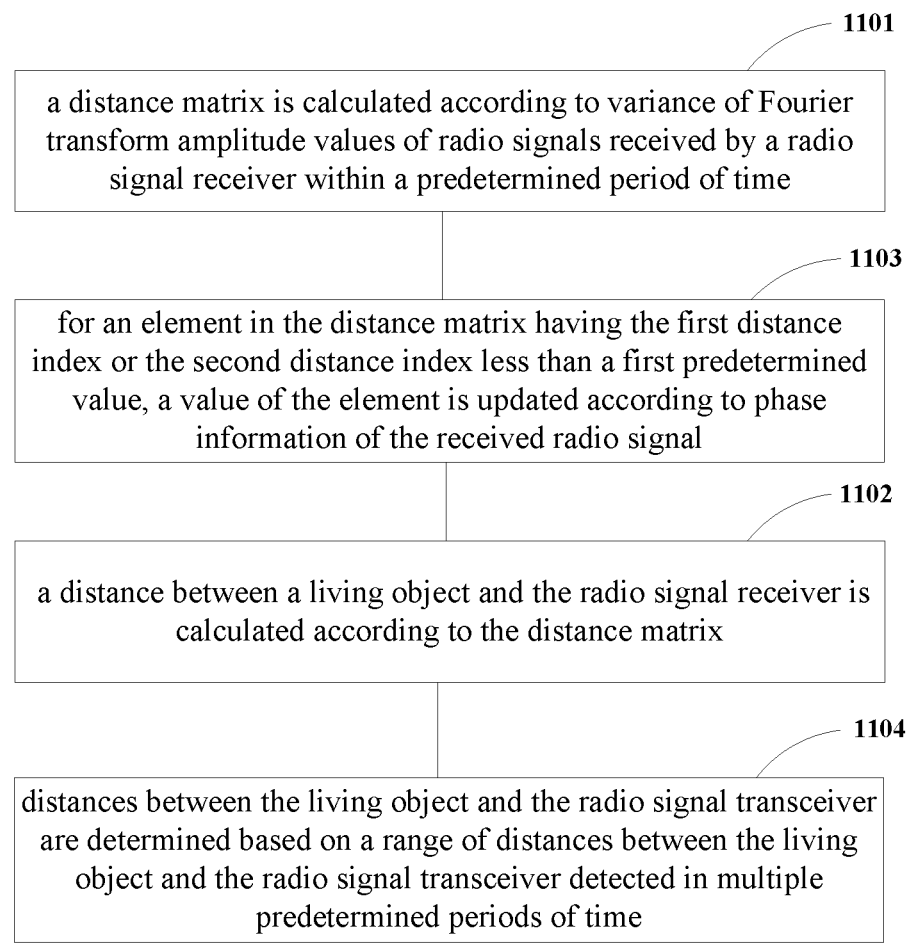
FIG. 11 is a flowchart of the living object detection method of Embodiment 2 of this disclosure.

FIG. 11 is a flowchart of the living object detection method of this embodiment. As shown in FIG. 11, the method includes:

block 1101: a distance matrix is calculated according to variance of Fourier transform amplitude values of radio signals received by a radio signal receiver within a predetermined period of time; and block 1102: a distance between a living object and the radio signal receiver is calculated according to the distance matrix.

As shown in FIG. 11, the method further includes:

block 1103: for an element in the distance matrix having the first distance index or the second distance index less than a first predetermined value, a value of the element is updated according to phase information of the received radio signal.

Figure 12:
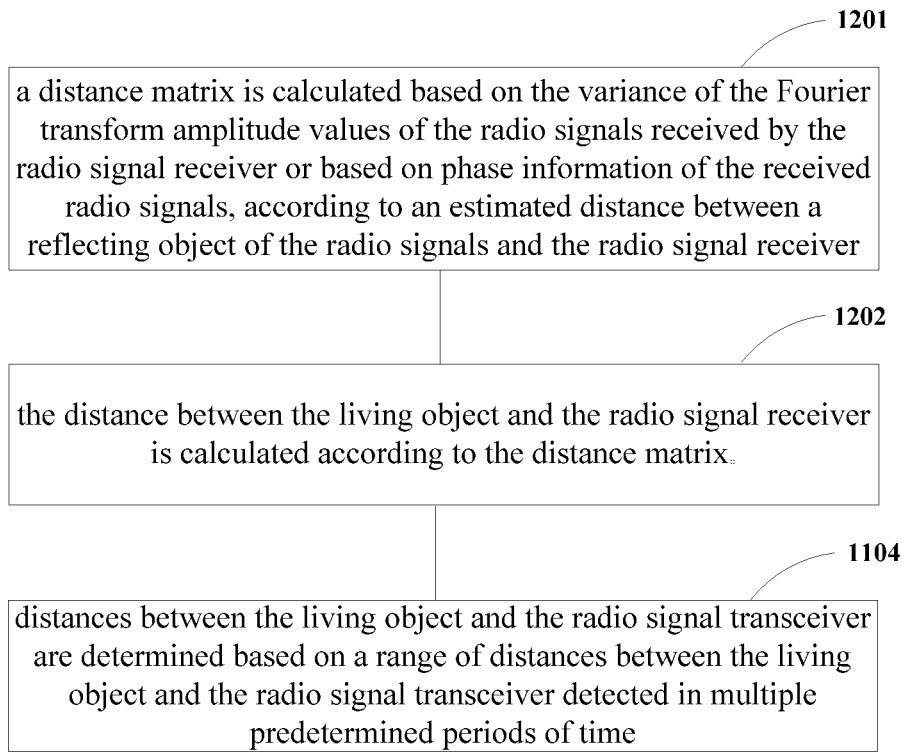
FIG. 12 is another flowchart of the living object detection method of Embodiment 2 of this disclosure.

FIG. 12 is another flowchart of the living object detection method of this embodiment. As shown in FIG. 12, the method includes:

block 1201: a distance matrix is calculated based on the variance of the Fourier transform amplitude values of the radio signals received by the radio signal receiver or based on phase information of the received radio signals, according to an estimated distance between a reflecting object of the radio signals and the radio signal receiver; and block 1202: the distance between the living object and the radio signal receiver is calculated according to the distance matrix.

In block 1201, for a case where the estimated distance is greater than the predetermined distance, the distance matrix is calculated based on the variance of the Fourier transform amplitude values of the received radio signals, and for a case where the estimated distance is less than or equal to the predetermined distance, the distance matrix is calculated based on the phase information of the received radio signals.

In this embodiment, the variance of the Fourier transform amplitude values of the received radio signals include a standard deviation std_fftVal between the Fourier transform amplitude values of the received radio signals.

In this embodiment, the calculating the distance matrix based on the variance of the Fourier transform amplitude values of the received radio signals includes: when an absolute value of a difference between the first distance index and the second distance index is less than a predetermined value n and greater than 0, granting a second predetermined value $\sigma 1$ for corresponding elements in the distance matrix when at least one of the following conditions is satisfied, the conditions including: the standard deviation between the Fourier transform amplitude values of the received radio signals to which the first distance index corresponds being greater than a third predetermined value $\theta 3$ and the standard deviation between the Fourier transform amplitude values of the received radio signals to which the second distance index corresponds being greater than the third predetermined value $\theta 3$; and a ratio of the standard deviation to which the first distance index corresponds to a mean value of the Fourier transform amplitude values of the radio signals received within the predetermined period of time to which the first distance index corresponds being greater than a fourth predetermined value $\beta 2$ and a ratio of the standard deviation to which the second distance index corresponds to a mean value of the Fourier transform amplitude values of the radio signals received within the predetermined period of time to which the second distance index corresponds being greater than the fourth predetermined value $\beta 2$.

In this embodiment, the phase information includes: a correlation between a phase of a distance to which the first distance index corresponds and a phase of a distance to which the second distance index corresponds within the predetermined period of time, and/or, a standard deviation between phases of the radio signals received within the predetermined period of time.

In this embodiment, the calculating a distance matrix based on phase information includes: when the absolute value of the difference between the first distance index and the second distance index is less than the predetermined value n and greater than 0, the standard deviation between the Fourier transform amplitude values of the received radio signals to which the first distance index corresponds is greater than a fifth predetermined value $\theta 1$ and the standard deviation between the Fourier transform amplitude values of the received radio signals to which the second distance index corresponds is greater than the fifth predetermined value $\theta 1$, granting a value denoting the correlation between the phases for corresponding elements in the distance matrix when at least one of the following conditions is satisfied, the conditions including: a standard deviation between phases of the received radio signals to which the first distance index corresponds being greater than a sixth predetermined value $\theta 2$ and a standard deviation between phases of the received radio signals to which the second distance index corresponds being greater than the sixth predetermined value $\theta 2$; and a value denoting the correlation between a phase of a distance to which the first distance index corresponds and a phase of a distance to which the second distance index corresponds being greater than a seventh predetermined value $\sigma$.

In this embodiment, n is a natural number, and a value of which is correlated with a distance resolution r of the radio signal receiver.

In this embodiment, block 1102 or block 1202 includes: when the number of pieces of continuous distribution of elements in the distance matrix having values greater than a predetermined value σ2 is greater than n/m, determining that there exists a living object in a distance range to which the continuously distributed elements correspond.

In this embodiment, block 1102 or block 1202 further includes: for elements in the distance matrix having values greater than the predetermined value σ2, the seventh predetermined value σ is granted to diagonal elements to which the elements correspond; and for elements in the distance matrix having values equal to the predetermined value σ2, when the number of elements in neighboring elements of the elements having values greater than the predetermined value σ2 is greater than or equal to an eighth predetermined value, values of the elements are updated by using a mean value of the elements in the neighboring elements having values greater than the predetermined value σ2.

As shown in FIGS. 11 and 12, the method further includes:

block 1104: distances between the living object and the radio signal transceiver are determined based on a range of distances between the living object and the radio signal transceiver detected in multiple predetermined periods of time.

In block 1104, in the range of distances detected in multiple predetermined periods of time, if a ratio of occurrence of the same distance range exceeds a threshold, it is determined that there exists a living object in the distance range; wherein, if a distance between center positions of two distance ranges is not greater than n*R, it is determined that the two distance ranges are the same distance range.

Reference may be made to description of corresponding units in Embodiment 1 for description of the blocks in this embodiment.

According to this embodiment and its variant, a position of a static living object may be detected, which is less dependent on scenarios, and is applicable to relatively wide ranges of scenarios.

Embodiment 3

Embodiment 3 of this disclosure provides an electronic device, including the living object detection apparatus as described in Embodiment 1.

Figure 13:
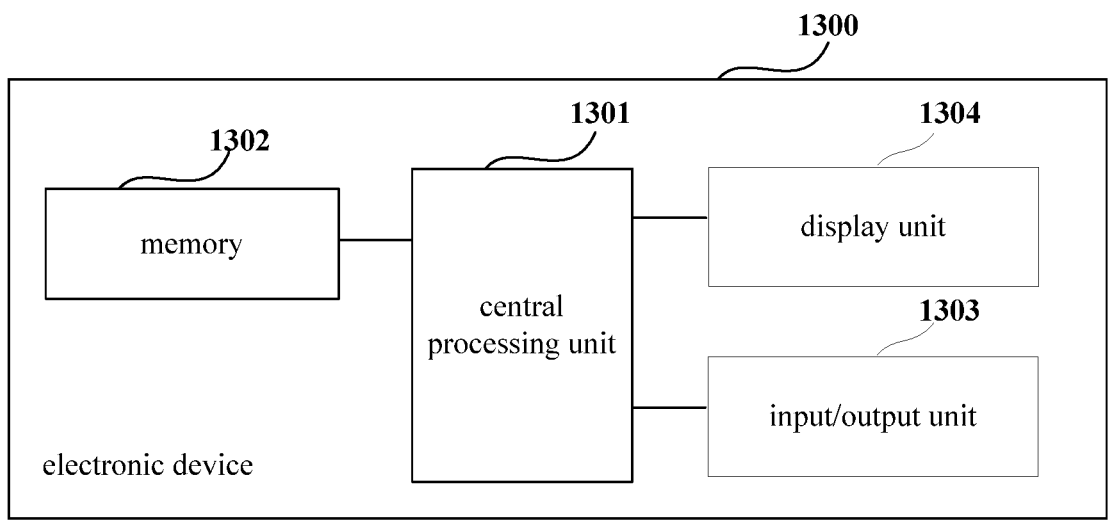
FIG. 13 is a schematic diagram of a structure of the electronic device of Embodiment 3 of this disclosure.

FIG. 13 is a schematic diagram of a structure of the electronic device of Embodiment 3 of this disclosure. As shown in FIG. 13, an electronic device 1300 may include a central processing unit (CPU) 1301 and a memory 1302, the memory 1302 being coupled to the central processing unit 1301. Wherein, the memory 1302 may store various data, and furthermore, it may store a program for control, and execute the program under control of the central processing unit 1301.

In one implementation, the functions of the detection apparatus 200 may be integrated into the central processing unit 1301.

The central processing unit 1301 may be configured to carry out the living object detection method described in Embodiment 2.

Furthermore, as shown in FIG. 13, the electronic device 1300 may include an input/output unit 1303, and a display unit 1304, etc.; wherein functions of the above components are similar to those in the related art, which shall not be described herein any further. It should be noted that the electronic device 1300 does not necessarily include all the parts shown in FIG. 13, and furthermore, the electronic device 1300 may include parts not shown in FIG. 13, and the related art may be referred to.

For example, the electronic device 1300 may include the radio signal transceiving device 110 of FIG. 1 to provide functions of transmission and reception of radio signals. Hence, the functions of the radio signal transceiving device 110 and the functions of the living object detection apparatus 200 (or 200a) may be integrated into the electronic device 1300.

An embodiment of the present disclosure provides a computer readable program code, which, when executed in a living object detection apparatus or an electronic device, will cause the living object detection apparatus or the electronic device to carry out the living object detection method as described in Embodiment 2.

An embodiment of the present disclosure provides a computer storage medium, including a computer readable program code, which will cause a living object detection apparatus or an electronic device to carry out the living object detection method as described in Embodiment 2.

The detection apparatuses described with reference to the embodiments of this disclosure may be directly embodied as hardware, software modules executed by a processor, or a combination thereof. For example, one or more functional block diagrams and/or one or more combinations of the functional block diagrams shown in FIGS. 2 and 8 may either correspond to software modules of procedures of a computer program, or correspond to hardware modules. Such software modules may respectively correspond to the blocks shown in FIG. 1. And the hardware module, for example, may be carried out by firming the soft modules by using a field programmable gate array (FPGA).

The soft modules may be located in an RAM, a flash memory, an ROM, an EPROM, and EEPROM, a register, a hard disc, a floppy disc, a CD-ROM, or any memory medium in other forms known in the art. A memory medium may be coupled to a processor, so that the processor may be able to read information from the memory medium, and write information into the memory medium; or the memory medium may be a component of the processor. The processor and the memory medium may be located in an ASIC. The soft modules may be stored in a memory of a mobile terminal, and may also be stored in a memory card of a pluggable mobile terminal. For example, if equipment (such as a mobile terminal) employs an MEGA-SIM card of a relatively large capacity or a flash memory device of a large capacity, the soft modules may be stored in the MEGA-SIM card or the flash memory device of a large capacity.

One or more functional blocks and/or one or more combinations of the functional blocks in FIGS. 2 and 8 may be realized as a universal processor, a digital signal processor (DSP), an application-specific integrated circuit (ASIC), a field programmable gate array (FPGA) or other programmable logic devices, discrete gate or transistor logic devices, discrete hardware component or any appropriate combinations thereof carrying out the functions described in this application. And the one or more functional block diagrams and/or one or more combinations of the functional block diagrams in FIGS. 2 and 8 may also be realized as a combination of computing equipment, such as a combination of a DSP and a microprocessor, multiple processors, one or more microprocessors in communication combination with a DSP, or any other such configuration.

This disclosure is described above with reference to particular embodiments. However, it should be understood by those skilled in the art that such a description is illustrative only, and not intended to limit the protection scope of the present disclosure. Various variants and modifications may be made by those skilled in the art according to the principle of the present disclosure, and such variants and modifications fall within the scope of the present disclosure.

For implementations of this disclosure containing the above embodiments, following supplements are further disclosed.

According to an aspect of an embodiment, a living object detection method, in which a living object is detected according to radio signals received by a radio signal receiver, the method including: calculating a distance matrix according to variance of Fourier transform amplitude values of radio signals received by a radio signal receiver within a predetermined period of time; and calculating a distance between a living object and the radio signal receiver according to the distance matrix; wherein the distance matrix has more than two elements, a value of each element denoting a probability of existence of a living object in a distance range to which the element corresponds, and the element having a first distance index (i) and a second distance index (j), the distance range to which the element corresponds being a smaller one of distances greater than or equal to a distance to which the first distance index corresponds and a distance to which the second distance index corresponds, and a larger one of distances less than or equal to the distance to which the first distance index corresponds and the distance to which the second distance index corresponds.

For an element in the distance matrix having the first distance index or the second distance index less than a first predetermined value, updating a value of the element according to phase information of the received radio signal.

A living object detection method, in which a living object is detected according to radio signals received by a radio signal receiver, the method including: calculating a distance matrix based on variance of the Fourier transform amplitude values of radio signals received by a radio signal receiver and according to an estimated distance between a reflecting object of the radio signals and the radio signal receiver, or calculating a distance matrix based on phase information of the received radio signals; and calculating the distance between the living object and the radio signal receiver according to the distance matrix; wherein the distance matrix has more than two elements, a value of each element denoting a probability of existence of a living object in a distance range to which the element corresponds, and the element having a first distance index (i) and a second distance index (j), the distance range to which the element corresponds being a smaller one of distances greater than or equal to a distance to which the first distance index corresponds and a distance to which the second distance index corresponds, and a larger one of distances less than or equal to the distance to which the first distance index corresponds and the distance to which the second distance index corresponds.

For a case where the estimated distance is greater than the predetermined distance, the distance matrix is calculated based on the variance of the Fourier transform amplitude values of the received radio signals; and for a case where the estimated distance is less than or equal to the predetermined distance, the distance matrix is calculated based on the phase information of the received radio signals.

The variance of the Fourier transform amplitude values of the received radio signals include: a standard deviation between the Fourier transform amplitude values of the received radio signals.

The calculating the distance matrix includes: when an absolute value of a difference between the first distance index and the second distance index is less than a predetermined value n and greater than 0, granting a second predetermined value σ1 for corresponding elements in the distance matrix when at least one of the following conditions is satisfied, the conditions including: the standard deviation between the Fourier transform amplitude values of the received radio signals to which the first distance index corresponds being greater than a third predetermined value θ3 and the standard deviation between the Fourier transform amplitude values of the received radio signals to which the second distance index corresponds being greater than the third predetermined value θ3; and a ratio of the standard deviation to which the first distance index corresponds to a mean value of the Fourier transform amplitude values of the radio signals received within the predetermined period of time to which the first distance index corresponds being greater than a fourth predetermined value β2 and a ratio of the standard deviation to which the second distance index corresponds to a mean value of the Fourier transform amplitude values of the radio signals received within the predetermined period of time to which the second distance index corresponds being greater than the fourth predetermined value β2.

The phase information includes: a correlation between a phase of a distance to which the first distance index corresponds and a phase of a distance to which the second distance index corresponds within the predetermined period of time, and/or, a standard deviation between phases of the radio signals received within the predetermined period of time.

The calculating the distance matrix includes: when the absolute value of the difference between the first distance index and the second distance index is less than the predetermined value n and greater than 0, the standard deviation between the Fourier transform amplitude values of the received radio signals to which the first distance index corresponds is greater than a fifth predetermined value θ1 and the standard deviation between the Fourier transform amplitude values of the received radio signals to which the second distance index corresponds is greater than the fifth predetermined value θ1, granting a value denoting the correlation between the phases for corresponding elements in the distance matrix when at least one of the following conditions is satisfied, the conditions including: a standard deviation between phases of the received radio signals to which the first distance index corresponds being greater than a sixth predetermined value θ2 and a standard deviation between phases of the received radio signals to which the second distance index corresponds being greater than the sixth predetermined value θ2; and a value denoting the correlation between a phase of a distance to which the first distance index corresponds and a phase of a distance to which the second distance index corresponds being greater than a seventh predetermined value σ.

According to an aspect of an embodiment, n is a natural number, and a value of which is correlated with a distance resolution r of the radio signal receiver.

The calculating the distance between the living object and the radio signal receiver includes: when the number of pieces of continuous distribution of elements in the distance matrix having values greater than a predetermined value σ2 is greater than n/m, determining that there exists a living object in a distance range to which the continuously distributed elements correspond.

For elements in the distance matrix having values greater than the predetermined value σ2, granting the seventh predetermined value σ to diagonal elements to which the elements correspond; and for elements in the distance matrix having values equal to the predetermined value σ2, when the number of elements in neighboring elements of the elements having values greater than the predetermined value σ2 is greater than or equal to an eighth predetermined value, updating values of the elements by using a mean value of the elements in the neighboring elements having values greater than the predetermined value σ2.

According to an aspect of an embodiment, determining distances between the living object and the radio signal transceiver is based on a range of distances between the living object and the radio signal transceiver detected in multiple predetermined periods of time.

In the range of distances detected in multiple predetermined periods of time, if a ratio of occurrence of the same distance range exceeds a threshold, it is determined that there exists a living object in the distance range; wherein, if a distance between center positions of two distance ranges is not greater than n*R, it is determined that the two distance ranges are the same distance range.

A living object detection apparatus, detecting a living object according to radio signals received by a radio signal receiver, the apparatus including: a fourth calculating unit configured to calculate a distance matrix based on variance of Fourier transform amplitude values of radio signals received by the radio signal receiver and according to an estimated distance between a reflecting object of the radio signals and the radio signal receiver, or calculate a distance matrix based on phase information of the received radio signals; and a fifth calculating unit configured to calculate a distance between the living object and the radio signal receiver according to the distance matrix; wherein the distance matrix has more than two elements, a value of each element denoting a probability of existence of a living object in a distance range to which the element corresponds, and the element having a first distance index and a second distance index, the distance range to which the element corresponds being a smaller one of distances greater than or equal to a distance to which the first distance index corresponds and a distance to which the second distance index corresponds, and a larger one of distances less than or equal to the distance to which the first distance index corresponds and the distance to which the second distance index corresponds.

The fourth calculating unit includes a sixth calculating unit and a seventh calculating unit; wherein, for a case where the estimated distance is greater than the predetermined distance, the sixth calculating unit calculates the distance matrix based on the variance of the Fourier transform amplitude values of the received radio signals; and for a case where the estimated distance is less than or equal to the predetermined distance, the seventh calculating unit calculates the distance matrix based on the phase information of the received radio signals.

The variance of Fourier transform amplitude values of received radio signals include: a standard deviation between the Fourier transform amplitude values of the received radio signals.

When an absolute value of a difference between the first distance index and the second distance index is less than a predetermined value n and greater than 0, the first calculating unit or the sixth calculating unit grants a second predetermined value σ1 for corresponding elements in the distance matrix when at least one of the following conditions is satisfied, the conditions including: the standard deviation between the Fourier transform amplitude values of the received radio signals to which the first distance index corresponds being greater than a third predetermined value θ3 and the standard deviation between the Fourier transform amplitude values of the received radio signals to which the second distance index corresponds being greater than the third predetermined value θ3; and a ratio of the standard deviation to which the first distance index corresponds to a mean value of the Fourier transform amplitude values of the radio signals received within the predetermined period of time to which the first distance index corresponds being greater than a fourth predetermined value β2 and a ratio of the standard deviation to which the second distance index corresponds to a mean value of the Fourier transform amplitude values of the radio signals received within the predetermined period of time to which the second distance index corresponds being greater than the fourth predetermined value β2.

The phase information includes: a correlation between a phase of a distance to which the first distance index corresponds and a phase of a distance to which the second distance index corresponds within the predetermined period of time, and/or, a standard deviation between phases of the radio signals received within the predetermined period of time.

When the absolute value of the difference between the first distance index and the second distance index is less than the predetermined value n and greater than 0, the standard deviation between the Fourier transform amplitude values of the received radio signals to which the first distance index corresponds is greater than a fifth predetermined value θ1 and the standard deviation between the Fourier transform amplitude values of the received radio signals to which the second distance index corresponds is greater than the fifth predetermined value θ1, the third calculating unit or the seventh calculating unit grants a value denoting the correlation between the phases for corresponding elements in the distance matrix when at least one of the following conditions is satisfied, the conditions including: a standard deviation between phases of the received radio signals to which the first distance index corresponds being greater than a sixth predetermined value θ2 and a standard deviation between phases of the received radio signals to which the second distance index corresponds being greater than the sixth predetermined value θ2; and a value denoting the correlation between a phase of a distance to which the first distance index corresponds and a phase of a distance to which the second distance index corresponds being greater than a seventh predetermined value σ.

The fifth calculating unit is configured to: when the number of pieces of continuous distribution of elements in the distance matrix having values greater than a predetermined value σ2 is greater than n/m, determine that there exists a living object in a distance range to which the continuously distributed elements correspond.

The invention claimed is:

1. An apparatus to detect an object among objects as a living object according to radio signals received by a radio signal receiver, the apparatus comprising:
a processor to couple to a memory and to,
calculate a distance matrix according to variance of Fourier transform amplitude values of the radio signals received by the radio signal receiver within a determined period of time; and
calculate a distance between the object and the radio signal receiver according to the distance matrix;

wherein
the distance matrix,
has two or more elements, a value of each element denoting a probability indicative of existence of the living object in a distance range to which the element corresponds,
the element having a first distance index and a second distance index, the distance range to which the element corresponds being greater than or equal to a smaller one of a distance to which the first distance index corresponds and a distance to which the second distance index corresponds, and less than or equal to a larger one the distance to which the first distance index corresponds and the distance to which the second distance index corresponds, and
when an absolute value of a difference between the first distance index and the second distance index is less than a determined value n and greater than 0, the processor is to grant a determined value of σ1 or σ2 for corresponding elements in the distance matrix, otherwise the processor is to grant the determined value of σ2 for corresponding elements in the distance matrix.

2. The apparatus according to claim 1, wherein the processor is to, for an element, among the elements, in the distance matrix having the first distance index or the second distance index less than a first determined value, update a value of the element according to phase information of the received radio signal.

3. The apparatus according to claim 1, wherein the variance of Fourier transform amplitude values of received radio signals comprise:
a standard deviation between the Fourier transform amplitude values of the received radio signals.

4. The apparatus according to claim 3, wherein,
when an absolute value of a difference between the first distance index and the second distance index is less than a determined value n and greater than 0,
the processor is to grant the determined value σ1 for corresponding elements in the distance matrix when at least any one or a combination of the following conditions is satisfied,
the standard deviation between the Fourier transform amplitude values of the received radio signals to which the first distance index corresponds being greater than a determined value θ3 and the standard deviation between the Fourier transform amplitude values of the received radio signals to which the second distance index corresponds being greater than the determined value θ3;
a ratio of the standard deviation to which the first distance index corresponds to a mean value of the Fourier transform amplitude values of the radio signals received within the determined period of time to which the first distance index corresponds being greater than a determined value β2 and a ratio of the standard deviation to which the second distance index corresponds to a mean value of the Fourier transform amplitude values of the radio signals received within the predetermined period of time to which the second distance index corresponds being greater than the determined value β2;
where, n is a natural number.

5. The apparatus according to claim 2, wherein the phase information comprises:

a correlation between a phase of a distance to which the first distance index corresponds and a phase of a distance to which the second distance index corresponds within the determined period of time, and/or, a standard deviation between phases of the radio signals received within the determined period of time.

6. The apparatus according to claim 5, wherein,
when the absolute value of the difference between the first distance index and the second distance index is less than the determined value n and greater than 0, a standard deviation between the Fourier transform amplitude values of the received radio signals to which the first distance index corresponds is greater than a determined value θ1 and the standard deviation between the Fourier transform amplitude values of the received radio signals to which the second distance index corresponds is greater than the determined value θ1,
the processor is to grant a value denoting the correlation between the phases for corresponding elements in the distance matrix when any one or combination of the following conditions is satisfied,
a standard deviation between phases of the received radio signals to which the first distance index corresponds being greater than a determined value θ2 and a standard deviation between phases of the received radio signals to which the second distance index corresponds being greater than the determined value θ2; and
a value denoting the correlation between a phase of a distance to which the first distance index corresponds and a phase of a distance to which the second distance index corresponds being greater than a determined value σ;
where, n is a natural number.

7. The apparatus according to claim 1, wherein the processor is to,
when an absolute value of a difference between the first distance index and the second distance index is less than a determined value n and greater than 0, and
when a continuous number of elements in the distance matrix with a value greater than the determined value σ2 is greater than n/m,
determine that there exists a living object, among the objects, in a distance range to which the continuous number of elements correspond;
where, n is a natural number and m is a natural number less than n.

8. The apparatus according to claim 7, wherein the processor is to,
for the elements in the distance matrix having values greater than the determined value σ2, grant the determined value σ to diagonal elements to which the elements correspond; and
for the elements in the distance matrix having values equal to the determined value σ2, when a number of the elements in neighboring elements of the elements having values greater than the determined value σ2 is greater than or equal to a second determined value, update values of the elements by using a mean value of the elements in the neighboring elements having values greater than the determined value σ2.

9. An electronic device, comprising the apparatus as claimed in claim 1.

10. A living object detection method, in which an object among objects is detected as a living object according to radio signals received by a radio signal receiver, the method comprising:
   calculating a distance matrix according to variance of Fourier transform amplitude values of the radio signals received by the radio signal receiver within a determined period of time; and
   calculating a distance between the object and the radio signal receiver according to the distance matrix;
   wherein,
      the distance matrix,
         has two or more elements, a value of each element denoting a probability indicative of existence of the living object in a distance range to which the element corresponds,
         the element having a first distance index and a second distance index, the distance range to which the element corresponds being greater than or equal to a smaller one of a distance to which the first distance index corresponds and a distance to which the second distance index corresponds, and being less than or equal to a larger one of the distance to which the first distance index corresponds and the distance to which the second distance index corresponds, and
   when an absolute value of a difference between the first distance index and the second distance index is less than a determined value n and greater than 0, the processor is to grant a determined value of σ1 or σ2 for corresponding elements in the distance matrix, otherwise the processor is to grant the determined value of σ2 for corresponding elements in the distance matrix.

* * * * *